(12) United States Patent
Ortiz et al.

(10) Patent No.: US 7,198,953 B2
(45) Date of Patent: Apr. 3, 2007

(54) METHOD OF USING A REFERENCE CONTROL COMPOSITION FOR MEASUREMENT OF NUCLEATED RED BLOOD CELLS

(75) Inventors: Nery Ortiz, Miami, FL (US); Jing Li, Miami, FL (US); Yi Li, Miami, FL (US); Sandra Socarras, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 10/960,370

(22) Filed: Oct. 7, 2004

(65) Prior Publication Data

US 2005/0079623 A1 Apr. 14, 2005

Related U.S. Application Data

(60) Provisional application No. 60/510,728, filed on Oct. 12, 2003.

(51) Int. Cl.
G01N 33/48 (2006.01)
G01N 31/00 (2006.01)

(52) U.S. Cl. .......................... 436/63; 436/10; 436/164; 436/166

(58) Field of Classification Search .................... 436/8, 436/10, 63, 164, 166; 435/2
See application file for complete search history.

(56) References Cited

U.S. PATENT DOCUMENTS

| | | | |
|---|---|---|---|
| 3,873,467 A | 3/1975 | Hunt | |
| 4,213,876 A | 7/1980 | Crews et al. | |
| 4,264,470 A | 4/1981 | Chastain et al. | |
| 4,299,726 A | 11/1981 | Crews et al. | |
| 4,358,394 A | 11/1982 | Crews et al. | |
| 4,389,490 A | 6/1983 | Crews et al. | |
| 4,405,719 A | 9/1983 | Crews et al. | |
| 4,704,364 A | 11/1987 | Carver et al. | |
| 5,125,737 A | 6/1992 | Rodriguez et al. | |
| 5,320,964 A | 6/1994 | Young et al. | |
| 5,512,485 A | 4/1996 | Young et al. | |
| 5,559,037 A | 9/1996 | Kim et al. | |
| 5,648,225 A | 7/1997 | Kim et al. | |
| 5,858,790 A | 1/1999 | Kim et al. | |
| 5,874,310 A | 2/1999 | Li et al. | |
| 5,917,584 A | 6/1999 | Li et al. | |
| 6,187,590 B1 | 2/2001 | Kim et al. | |
| 6,200,500 B1 | 3/2001 | Ryan | |
| 6,221,668 B1 | 4/2001 | Ryan et al. | |
| 6,399,388 B1 | 6/2002 | Ryan et al. | |
| 6,403,377 B1 | 6/2002 | Ryan et al. | |
| 6,406,915 B2 | 6/2002 | Ryan et al. | |
| 6,410,330 B1 | 6/2002 | Li et al. | |
| 6,448,085 B1 | 9/2002 | Wang et al. | |
| 6,472,215 B1 | 10/2002 | Huo et al. | |
| 6,514,763 B2 | 2/2003 | Carver et al. | |
| 6,569,682 B2 | 5/2003 | Elliott et al. | |
| 6,573,102 B2 | 6/2003 | Li et al. | |
| 6,653,063 B2 | 11/2003 | Carver et al. | |
| 6,653,137 B2 | 11/2003 | Ryan | |
| 6,673,618 B1 | 1/2004 | Li et al. | |
| 6,723,563 B2 | 4/2004 | Ryan | |
| 2001/0046708 A1 | 11/2001 | Carver et al. | |
| 2003/0104630 A1 | 6/2003 | Ryan | |

OTHER PUBLICATIONS

Beckman Coulter Bulletin 9165, Clincial Case Studies, Coulter GEN-S System Enhanced VCS Technology, pp. 1-32, copyright 2000.*
Coulter LH 700 Series System Reference, PN4277248 (Oct. 2003), cover page and pp. v-x, 1-1 to 1-6, 3-1, and 3-14 to 3-17.

* cited by examiner

*Primary Examiner*—Maureen M. Wallenhorst
(74) *Attorney, Agent, or Firm*—Cuspa Technology Law Associates; Mitchell E. Alter

(57) ABSTRACT

Methods of using a reference control composition containing a nucleated red blood cell component for measurement of nucleated red blood cells are disclosed. The nucleated red blood cell component is made of stabilized or processed nucleated blood cells which have impedance and optical properties simulating the impedance and optical properties of human nucleated red blood cells under a blood lysing condition as measured by a specific measurement. The methods include mixing the reference control composition with a lytic reagent, and analyzing the control sample mixture on a flow cytometric instrument by impedance, impedance and optical measurement, or DC impedance and a multi-dimensional measurement of light scatter, radio frequency and a second DC impedance; and reporting the simulated nucleated red blood cells in the reference control composition.

22 Claims, 4 Drawing Sheets

METHOD OF USING A REFERENCE CONTROL COMPOSITION FOR MEASUREMENT OF NUCLEATED RED BLOOD CELLS

CROSS-REFERENCE TO RELATED APPLICATION

This application claims the benefit under 35 USC 119 (e) of the provisional patent application Ser. No. 60/510,728, filed on Oct. 12, 2003, which is herein incorporated by reference in its entirety.

FIELD OF THE INVENTION

The present invention relates to a method of making and using a reference control composition for determination of nucleated red blood cells of a blood sample on a flow cytometric instrument. More specifically the reference control composition is suitable for a method of differentiation of nucleated red blood cells from other cell types in a blood sample by impedance and optical measurements and combination thereof.

BACKGROUND OF THE INVENTION

Quality control has long been a necessary and routine procedure in clinical hematology. Accuracy in the counting of various types of blood cells is dependent, in part, upon the use of adequate control products and methods of using the control products. With the numerous types of equipment for particle counting now available, quality control by the use of control products is necessary, since the possibility of an instrument malfunctioning is ever present. The traditional method of maintaining a quality control program for automatic particle counting equipment has consisted of providing fresh human blood as a whole blood standard. However, this fresh blood is usable for only one day, therefore, various manufactured control products which have longer product lifetime have been developed.

Commonly used particles in a control product simulate or approximate the types of particles or cells that are intended to undergo analysis. Consequently, these particles have been frequently referred to as analog particles. The analog particles should be selected or designed so that they have certain characteristics that are similar to those of the particles or cells to be analyzed in the instruments. Exemplary characteristics and parameters include similarities in size, volume, surface characteristics, granularity properties, light scattering properties and fluorescence properties.

Various commercial reference control products are now available, which use various processed or fixed human or animal blood cells as analogs of human blood cells. U.S. Pat. No. 5,512,485 (to Young et al) teaches a hematology control comprising several white blood cell analogs made of processed and fixed animal red blood cells. U.S. Pat. Nos. 6,187,590 and 5,858,790 (to Kim et al) teach a hematology control comprising a nucleated red blood cell (NRBC) analog made of lysed and fixed avian or fish red blood cells. U.S. Pat. Nos. 6,406,915, 6,403,377, 6,399,388, 6,221,668, and 6,200,500 (to Ryan, et al) teach a hematology control comprising a NRBC analog derived from avian blood cells. U.S. Pat. No. 6,448,085 (to Wang et al) teaches a hematology control comprising a nucleated red blood cell (NRBC) analog derived from chicken blood and fixed human blood with nucleated red blood cells. U.S. Pat. Nos. 6,653,137 and 6,723,563 (to Ryan) teach methods of making and using a hematology reference control which contains a nucleated red blood cell component made by lysing and removing cytoplasm from reptile or fish blood cells.

In addition, several detection methods for measuring nucleated red blood cells in a blood sample on a hematology instrument have been reported. U.S. Pat. Nos. 5,874,310 and 5,917,584 (to Li et al) teach a method of differentiating nucleated red blood cells by measuring two angles of light scatter signals of a blood sample under lysing condition without the requirement of using fluorescence analysis. U.S. Pat. Nos. 5,874,310 and 5,917,584 further teach a method of differentiating nucleated red blood cells by measuring light scatter and DC impedance signals. U.S. Pat. No. 6,410,330 (to Li et al) and co-pending patent application U.S. Ser. No. 10/226,800 (to Li et al) provide a method of determining NRBC by using DC impedance measurement.

U.S. Pat. No. 6,472,215 (to Huo et al) teaches a method of differentiating nucleated red blood cells by lysing a first aliquot and a second aliquot of a blood sample separately with a first lysing reagent system and a second lysing reagent system; measuring the first sample mixture in a flow cell by DC impedance, radio frequency, and light scatter measurements; measuring cell distributions and counting remaining blood cells in the second sample mixture by DC impedance measurements in a non-focused flow aperture; analyzing blood cell distribution patterns obtained from measuring the first sample mixture and from measuring the second sample mixture respectively; and further performing a combined analysis to differentiate NRBCs from other cell types and to determine numbers of NRBCs in the blood sample.

It is desirable to provide a reference control containing a nucleated red blood cell component for each of the above described measurement methods for quality control of the instruments.

It is also desirable to use a cell based nucleated red blood cell analog in a reference control, wherein the cell based analogs simulate the properties of nucleated red blood cell population under specific reaction conditions and detection conditions.

SUMMARY OF THE INVENTION

In one embodiment, the present invention is directed to a method of using a reference control which contains a nucleated red blood cell component for measurement of nucleated red blood cells. The method comprises the steps of: (a) providing a reference control composition to a flow cytometric instrument capable of measuring nucleated red blood cells by an impedance measurement, the reference control composition comprising a nucleated red blood cell component made of stabilized animal nucleated red blood cells; wherein the stabilized animal nucleated red blood cells have impedance properties simulating impedance properties of human nucleated red blood cells under a blood lysing condition as measured by the impedance measurement; (b) mixing the reference control composition with a lytic reagent to form a control sample mixture; wherein upon exposing to the lytic reagent the stabilized animal nucleated red blood cells are substantially lysed and cellular volume thereof reduce to substantially nuclear volume; (c) analyzing the control sample mixture by the impedance measurement to measure the substantially lysed animal nucleated red blood cells from step (b); and (d) reporting numbers of simulated human nucleated red blood cells in the reference control composition.

Herein the impedance measurement includes direct current (DC) and radio frequency (RF) impedance measurement.

The stabilized animal nucleated red blood cells have a mean cell volume from about 380 fl to about 460 fl, preferably are reptile red blood cells or fish red blood cells, more particularly alligator red blood cells.

The reference control composition can further comprise white blood cell, red blood cell and platelet components, and the method can further comprise measuring and reporting white blood cells, red blood cells and platelets.

In a further embodiment, the method comprise the steps of: (a) providing a reference control composition to a flow cytometric instrument capable of measuring nucleated red blood cells by impedance and optical measurements, the reference control composition comprising a nucleated red blood cell component made of stabilized animal nucleated red blood cells; wherein the stabilized animal nucleated red blood cells have impedance and optical properties simulating impedance and optical properties of human nucleated red blood cells under a blood lysing condition as measured by the impedance and optical measurements; (b) mixing the reference control composition with a lytic reagent to form a control sample mixture; wherein upon exposing to the lytic reagent the stabilized animal nucleated red blood cells are substantially lysed and cellular volume thereof reduce to substantially nuclear volume; (c) analyzing the control sample mixture by the impedance and optical measurements to measure the substantially lysed animal nucleated red blood cells from step (b); and (d) reporting numbers of simulated human nucleated red blood cells in the reference control composition.

Herein the impedance measurement includes direct current (DC) and radio frequency (RF) impedance measurement, and the optical measurement includes light scatter measurement and axial light loss measurement.

In another embodiment, the method comprises the steps of: (a) providing a reference control composition comprising a nucleated red blood cell component made of stabilized animal nucleated red blood cells; wherein the stabilized animal nucleated red blood cells have DC impedance, radio frequency, and light scatter properties simulating DC impedance, radio frequency, and light scatter properties of human nucleated red blood cells under a blood lysing condition as measured by the DC impedance, radio frequency, and light scatter measurements; (b) exposing a first aliquot of the reference control composition to a first lysing reagent system to lyse red blood cells and to form first control sample mixture; (c) exposing a second aliquot of the reference control composition to a second lysing reagent system to lyse red blood cells and to form second control sample mixture; wherein upon exposing to the first and second lytic reagent systems the stabilized animal nucleated red blood cells are substantially lysed and cellular volume thereof reduce to substantially nuclear volume; (d) measuring the first control sample mixture in a flow cell by a detection comprising a first direct current impedance measurement (DC1), radio frequency impedance measurement (RF), and a median angle light scatter measurement (LS); (e) measuring blood cell distributions of the second control sample mixture by a second direct current impedance measurement (DC2); (f) analyzing measurements of steps (d) and (e); and (g) reporting simulated nucleated red blood cells in the reference control composition.

In a further aspect, the present invention is directed to reference control compositions containing a nucleated red blood cell component. In one embodiment, the reference control composition comprises a predetermined volume of an analog suspension comprising stabilized animal nucleated red blood cells suspended in a suspension medium, and a predetermined volume of a human whole blood, wherein the suspension medium is compatible with the human whole blood such that blood cells of the human whole blood in the composition behave substantially the same to blood cells of the human whole blood prior to mixing with the analog suspension in an analysis on a flow cytometric instrument. The stabilized nucleated red blood cells are animal nucleated red blood cells, preferably reptile and fish red blood cells.

In another embodiment, the reference control composition comprises a nucleated red blood component made of small mammalian lymphocytes having nuclear size in a range from about 4.0 μm to about 4.7 μm, suspended in a cell suspension medium, wherein the cytoplasm of the small mammalian lymphocytes are substantially removed, and remaining cellular entity is fixed.

DETAILED DESCRIPTION OF THE INVENTION

Figure 1:
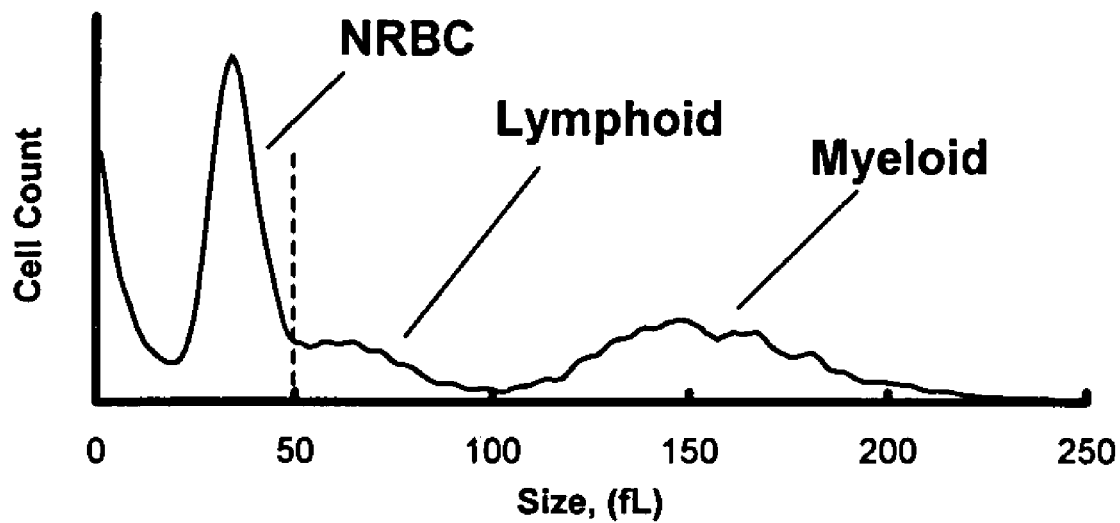
FIG. 1 shows a histogram of a clinical whole blood sample obtained using a DC impedance measurement.

1. Reference Control Composition Containing a Nucleated Red Blood Cell Component and the Method of Making In one embodiment, the present invention provides a method of making a reference control composition that contains a nucleated red blood cell (NRBC) component. The method comprises the steps of: providing a nucleated blood cell suitable for simulating a human nucleated red blood cell under a lysing condition as measured by a specific measurement or a specific combination of measurements; stabilizing the nucleated blood cell; then admixing the stabilized nucleated blood cell in a suspension medium suitable for delivering the reference control composition to a flow cytometric analyzer for analysis of nucleated red blood cells. For the purpose of the present invention, the nucleated red blood cell component, as well as other cell type components, are also referred to as analogs, for example, NRBC analogs.

Suitable examples of nucleated blood cells suitable for simulating human nucleated red blood cells include various nucleated animal red blood cells and small mammalian lymphocytes. Preferably reptile and fish red blood cells, such as alligator, shark and salmon red blood cells, are used. Nucleated red blood cells from different animal species have different cellular and nuclear volumes or sizes. For example, chicken red blood cells are substantially smaller than alligator and shark red blood cells. Although lysed and fixed chicken red blood cells have been used as NRBC analogs for fluorescent based measurement, these cells are too small to simulate human nucleated red blood cells when the measurement method is based on sizing. For example, when impedance or light scatter only measurement are used, these analogs can be outside of the dynamic range of the measurement provided for human blood analysis.

Alligator and shark red blood cells have large nuclear volumes. When exposed to a lytic reagent used for sample preparation, they are substantially lysed and the cellular volumes reduce down to substantially their nuclear volumes which closely resemble human nucleated red blood cells under the same reaction condition. Furthermore, these substantially lysed alligator or shark red blood cells can also simulate certain optical properties of human nucleated red blood cells under the same reaction condition, for example, light scatter properties, and axial light loss properties. In a preferred embodiment, alligator red blood cells are used for making the nucleated red blood cell component because of the availability of alligator whole blood.

Moreover, it is known that cellular and nuclear volumes of alligator red blood cells can be different depending on the age of the alligator and their food intake. For example, the alligators fed with fresh meat have relatively larger red blood cells than those fed with processed dry food. It has been found for the purpose of the present invention that the alligator red blood cells having a mean cell volume from about 380 fl to about 460 fl are suitable for simulating human nucleated red blood cells as measured by impedance and optical measurements described hereinafter.

To prepare the nucleated red blood cell component, the alligator red blood cells in a quantity of alligator whole blood is separated first from other blood components including white blood cells, platelets and plasma by centrifugation. The alligator red blood cells are then washed by an isotonic wash solution. The washed alligator red blood cells are suspended in a stabilizing suspension medium for storage and use on a flow cytometric instrument. One suitable wash solution is the phosphate buffered saline solution (PBS). Suitable examples of the stabilizing suspension media include phosphate buffered saline solution and an aqueous solution of a plasma substance. As defined herein, an aqueous solution of a plasma substance comprises an aqueous solution of a serum substance, serum substance in combination with a plasma protein and mixtures thereof. The serum substance comprises an aqueous solution of serum lipid. As defined herein, serum lipid comprises cholesterol, cholesterol esters and cholesterol which has been combined with one or more other compounds found in serum plasma and mixtures thereof. Preferably, such other compounds further comprise lipoproteins and phospholipids, and mixtures thereof. As appreciated by those skilled in the art, typically, cholesterol will contain approximately 30% esters. Preferably, the serum substance in the pretreatment is selected from the group comprising cholesterol, cholesterol esters, lipoprotein cholesterol, lipoprotein cholesterol esters, cholesterol combined with phospholipids and mixtures thereof. A suitable commercially available example of cholesterol in combination with phospholipids is Pentex® Cholesterol Super-Trate by Miles, Inc., which is a high density lipoprotein cholesterol and lipoprotein cholesterol esters in combination with phospholipids. As further defined herein, plasma protein comprises one or more of the proteins contained in plasma. Preferably, such plasma proteins comprise albumin, lipoproteins, globulins, fibrinogens and mixtures thereof. The stability suspension media may contain other ingredients known to those skilled in the art to confer long term stability. Other examples of suitable media are more fully described in U.S. Pat. Nos. 4,213,876, 4,299,726, 4,358,394, 3,873,467, 4,704,364, 5,320,964, 5,512,485 and 6,569,682 which are herein incorporated by reference in their entirety.

The following specific example is disclosed in U.S. Pat. No. 4,299,726:

| Stabilizing Suspension Media for Conferring Long Term Cell Stability Approximate Amounts Liter Formulation | |
|---|---|
| 1. Distilled water | 500 ml |
| 2. Propyl paraben | 0.3 to 1.0 gm |
| 3. Methyl paraben | 0.5 to 1.0 gm |
| 4. Procaine hydrochloride | 0.1 to 0.5 gm |
| 5. Deoxycholic acid | 0.1 to 0.9 gm |
| 6. Lactose | 10.0 to 50.0 gm |
| 7. Actidione | 0.1 to 0.6 gm |
| 8. Trisodium citrate dehydrate | 3.0 to 8.0 gm |
| 9. Citric acid monohydrate | 0.3 to 0.9 gm |
| 10. Sodium dihydrogen phosphate monohydrate | 0.8 to 2.5 mg |
| 11. Phenergan hydrochloride | 0.1 to 1.0 gm |
| 12. Colistimethate, sodium | 0.2 to 0.9 gm |
| 13. Penicillin G., sodium | $0.5 \times 10^6$ to $3 \times 10^6$ units |
| 14. Kanamycin sulfate | 0.2 to 0.8 gm |
| 15. Neomycin sulfate | 0.2 to 1.0 gm |
| 16. 5'-AMP | 0.4 to 1.0 gm |
| 17. Adenine | 0.2 to 0.8 gm |
| 18. Inosine | 0.4 to 1.0 gm |
| 19. Dihydrostreptomycin sulfate | 0.2 to 1.0 gm |
| 20. Tetracycline hydrochloride | 0.2 to 1.0 gm |
| 21. 30% Bovine albumin | 100 to 350 ml |
| 22. q.s. to 1 liter with distilled water | |

Furthermore, the following medium is disclosed by U.S. Pat. No. 6,569,682, which provides extended stability of the reference control composition.

| Stabilizing Suspension Medium Approximate Amounts Liter Formulation | | |
|---|---|---|
| Component | Range (grams/liter) | Preferred Range (grams/liter) |
| Xanthine compound | 1–10 | 2–7 |
| Adenosine monophosphate | 0.1–1.0 | 0.2–0.8 |
| Inosine | 0.1–1.0 | 0.2–0.8 |
| pH adjusting agents sufficient to obtain | pH 5.8–6.8 | pH 6.0–6.5 |
| Osmolality adjusters sufficient to obtain | 200–400 mOsm | 250–350 |
| Preservative | effective amount | 2.0–6.0 |
| Water | fill to 1 liter | |

Since many of the chemicals listed above are known commercially by several names, the name given is a common name listed in the Merck Index, published by Merck and Co., Inc., Rahway, N.J.

Example 1 illustrates an exemplary process of preparing the nucleated red blood cell component using alligator red blood cells. A reference control composition containing the prepared nucleated red blood cell component was utilized for nucleated red blood cell measurement using various measurement methods, as illustrated in Examples 5 to 7.

In another embodiment, small mammalian lymphocytes from whole blood or produced in vitro by a suitable cell line can be used for making the nucleated red blood cell component. The small mammalian lymphocytes suitable for making the nucleated red blood cell component have a nuclear size in a range from about 4.0 µm to about 4.7 µm. The nuclear size can be measured under a lysing condition on a hematology instrument capable of differentiating lymphocytes from other cell types. When small mammalian lymphocytes are used, it is preferred to treat the lymphocytes to substantially remove the cytoplasm to reduce the cellular volume substantially to their nuclear volume, and then fix the remaining cellular entity. The term of "remaining cellular entity" refers to the small mammalian lymphocytes upon substantially removing the cytoplasm, which may partially maintain the cellular membrane. The treatment can involve exposing the small mammalian lymphocytes to a lytic reagent for a certain period of time. The lytic reagent permeates cellular membrane, resulting in removal of the cytoplasm. The processed small mammalian lymphocytes simulate the size and optical properties of human nucleated red blood cells under lysing condition as measured by impedance and optical measurements as described hereinafter.

Various lytic reagents known in the art for lysing blood cells can be used for treating the small mammalian lymphocytes. One suitable example is a lytic reagent containing a quaternary ammonium surfactant represented by following molecular structure:

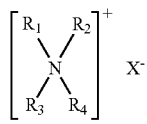

wherein $R_1$ is an alkyl, alkenyl or alkynyl group having 12 to 16 carbon atoms; $R_2$, $R_3$ and $R_4$ are alkyl groups having 1 to 4 carbon atoms and $X^-$ is chloride or bromide anion. Another example is a lytic reagent containing saponin. The remaining cellular entity upon substantially removing the cytoplasm can be fixed with a fixative solution. Suitable examples of the fixative include, but are not limited to, an aldehyde fixative, such as paraformaldehyde, formaldehyde and glutaraldehyde.

In a further embodiment, the reference control composition further includes a white blood cell component which simulates a white blood cell (WBC) under a specific detection condition. In the presence of a white blood cell component, a ratio between the NRBC component and the white blood cell component can be used to report the numbers of NRBCs per 100 WBC, which is the same unit used for reporting nucleated red blood cells in a blood sample in clinical laboratories. Preferably, the white blood cell component or analog has properties similar to one major white blood cell subpopulation, such as granulocytes or lymphocytes.

Furthermore, the white blood cell component can include more than one white blood cell subcomponents, for example, two, three, four or five white blood cell subcomponents, or analogs, to simulate multiple white blood cell subpopulations for a white blood cell differential analysis. Suitable examples of white blood cell analogs include stabilized and fixed mammalian white blood cells, and processed and/or fixed human and animal red blood cells, as known in the art. In one embodiment, the white blood cell subcomponents can be made from processed goose and alligator red blood cells for differential analysis using a combination of impedance and light scatter measurement, as taught in U.S. Pat. Nos. 5,320,964 and 5,512,485, which are herein incorporated by reference in their entirety. In another embodiment, the white blood cell subcomponents can be made from processed avian and human red blood cells for differential analysis using an impedance measurement, as taught in U.S. Pat. No. 4,704,364, which is herein incorporated by reference in its entirety. In a further embodiment, the white blood cell subcomponents can be made from fixed mammalian white blood cells. The mammalian white blood cells are fixed prior to lysing the red blood cells in the whole blood during the preparation of the white blood cell subcomponents.

Optionally, the mammalian white blood cells and the human and animal red blood cells can be further treated by contacting with a lipoprotein during the process of preparing the white blood cell subcomponents. The contact with lipoprotein can occur prior to fixing the white or red blood cells, it can also occur after fixing and during storage in the suspension medium, as taught in U.S. Pat. Nos. 5,320,964, 5,512,485, 6,406,915, 6,403,377, 6,399,388, 6,221,668, and 6,200,500 which are incorporated herein by reference in their entirety.

In another embodiment, the present invention provides a reference control composition which comprises the above described nucleated red blood cell component, a white blood cell component, and additionally a red blood cell component and a platelet component in the suspension medium.

The red blood cell component can be stabilized human or animal red blood cells, preferably, stabilized human red blood cells. The process of making red blood cell component has been described in detail in U.S. Pat. Nos. 4,299,726 and 4,358,394, which are incorporated by references in their entirety. The platelet component can be stabilized human or animal platelets, or platelet analogs made from other cell types. One suitable example is using processed goat red blood cells as the platelet analog, as disclosed in U.S. Pat. Nos. 4,264,470, 4,389,490 and 4,405,719.

The red blood cells of a blood sample or the stabilized human red blood cells in the reference control composition are lysed under lysing conditions normally used for preparing a blood sample for the measurement of nucleated red blood cells and white blood cells, and should not be detected in the measurement if the analyzer operates properly. The platelets of a blood sample under the lysing conditions reduce in size and they are either below the detection threshold for the measurement of nucleated red blood cells, or are separated from the nucleated red blood cells. The platelet analogs described above simulate the response of the platelets of a blood sample under the lysing condition. Therefore, the red blood cell component and platelet component in the reference control composition further reflect the response of the control composition to the lysing reagent, as well as the reaction conditions on the instrument. Hence, the reference control composition containing red blood cell and platelet components can provide further information relating to instrument operating conditions.

Moreover, the reference control composition containing red blood cells and platelets can also be used for the red blood cell and platelet measurements, which are commonly performed together with measurements of the white blood cells and nucleated red blood cells on an automated hematology analyzer.

Example 2 illustrates a preparation of a reference control composition containing a nucleated red blood cell component, a white blood cell component, a red blood cell component and a platelet component. This reference control composition was utilized for enumeration of nucleated red blood cells using a DC impedance measurement as shown in Example 5.

Example 3 illustrates a reference control composition containing a nucleated red blood cell component, multiple white blood cell analogs, as well as a red blood cell component and a platelet component. This reference control composition was utilized for the measurement of nucleated red blood cells and differential analysis of white blood cells.

In a further embodiment, the present invention provides a hematology control system which comprises a series of reference control compositions containing a nucleated red blood cell component. Among the series, each composition has an increasing concentration of the nucleated red blood cell analogs, but a constant concentration of the white blood cell component. This control system is used for determining linear response of the nucleated red blood cell enumeration method on a flow cytometric instrument, hence, it is also referred to as a linearity control.

Example 4 illustrates an example of the linearity control which contains a nucleated red blood cell component, a white blood cell component, a red blood cell component and a platelet component. As illustrated, the nucleated red blood cell component was made of stabilized alligator red blood cells and the white blood cell component was made of fixed goose red blood cells. In Example 4, a single white blood cell component was used. However, multiple white blood cell subcomponents described in Example 3 can also be used for making a linearity control for nucleated red blood cell measurement.

In an alternative embodiment, a reference control composition can also be provided by mixing the nucleated red blood cell analogs with a fresh human whole blood sample. This control composition can be prepared prior to running it on the flow cytometric instrument. A linearity control can also be made by adding a series of nucleated red blood cell analogs in a varying amounts into a series of a constant predetermined volume of a fresh human whole blood. Using this method, the suspension medium of the nucleated red blood cell analogs needs to be compatible with the whole blood, so that the blood cells of the whole blood maintain their property when analyzed on the flow cytometric instrument. It has been found that the suspension media disclosed in U.S. Pat. Nos. 4,299,726, 4,704,364, 5,320,964 and 5,512,485 are suitable for use with whole blood.

Example 6 illustrates the use of a reference control composition containing nucleated red blood cell analogs in a whole blood for the measurement of nucleated red blood cells and white blood cells. It has also been found that this reference control composition can also be used on a flow cytometer for measurements of nucleated red blood cells and white blood cells using fluorescent measurements.

2. The Method of Using the Reference Control Composition for the Measurement of Nucleated Red Blood Cells In another aspect, the present invention provides methods of using the reference control composition containing a nucleated red blood cell component for the measurement of nucleated red blood cell using various measurement methods.

In one embodiment, the present invention provides a method of using the reference control composition containing a nucleated red blood cell component for the measurement of nucleated red blood cell using an impedance measurement. The impedance measurement includes direct current (DC) impedance and radio frequency (RF) impedance measurements. The method and instrumentation used for DC impedance measurement were described in U.S. Pat. No. 6,410,330, which is herein incorporated by reference in its entirety. It is noted that the DC impedance measurement can be made using a non-focused flow aperture, or a focused flow cell. The RF impedance measurement is preferred to be made using a focused flow cell.

Figure 2:
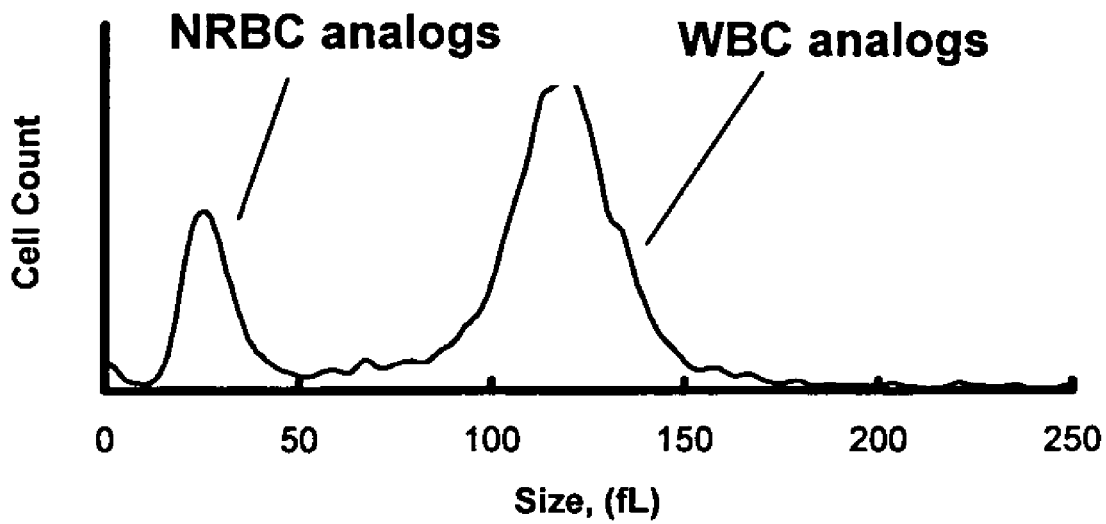
FIG. 2 shows a histogram of the reference control of Example 2, which contained a nucleated red blood cell component made of stabilized alligator red blood cells and a white blood cell component made of fixed goose red blood cells.

Example 5 illustrates an example using the reference control composition of Example 2 for measurement of nucleated red blood cells using a DC impedance measurement. FIG. 1 shows an obtained histogram of a clinical whole blood sample which contained about 22 NRBCs per 100 WBC. As shown, the nucleated red blood cells appeared as a distinct peak on the left of the histogram and white blood cells appeared on the right side of the nucleated red blood cells. FIG. 2 shows the obtained histogram of the reference control composition of Example 2, which contained a nucleated red blood cell component made of stabilized alligator red blood cells and a white blood cell component made of fixed goose red blood cells. As shown, the stabilized alligator red blood cells closely resembled human nucleated red blood cells and they were clearly separated from the WBC analogs. The obtained histogram was post analyzed, and the ratio between the NRBC analogs and the WBC analogs was reported as numbers of NRBC per 100 WBC.

Figure 3:
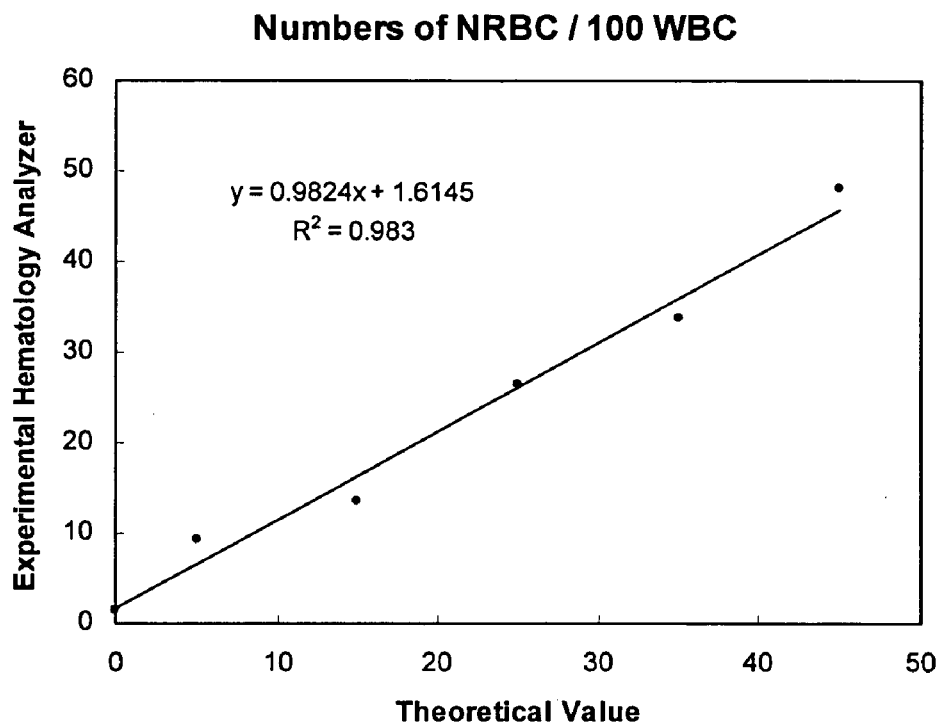
FIG. 3 shows a correlation between the theoretical value of the NRBC concentration of the reference control composition of Example 4 and the results obtained by DC impedance measurement.

The linearity control of Example 4 was measured on the modified LH750 hematology analyzer as described in Example 5. The numbers of NRBC per 100 WBC obtained from the histograms were plotted against the theoretical value obtained from the NRBC analog and WBC analog concentrations. As shown in FIG. 3, the measured NRBC concentrations of the reference controls had an excellent linear correlation with the theoretical values within the concentration range measured.

In another embodiment, the present invention provides a method of using the reference control composition containing a nucleated red blood cell component for the measurement of nucleated red blood cell using light scatter measurement. The measurement method and instrumentation used for the measurement were described in detail in U.S. Pat. Nos. 5,874,310 and 5,917,584, which are herein incorporated by reference in their entirety.

The differential analysis of nucleated red blood cells is performed in a focused flow cell using light scatter measurements. When a particle, such as a blood cell, passes through the aperture of a flow cell, it scatters the incident light from a laser beam in all directions. The light scatter signals can be detected by a light detector at various angles relative to the incident light beam between 0° to 180°. It has been found that each cell population has different light scattering properties, either significant or minor, which can be utilized for differentiation of different cell populations. The light scatter signals detected in less than 10° from the incident light are commonly called low angle light scatter. The light scatter signals detected from about 10° to about 70° from the incident light are called medium angle light scatter, and the light scatter signals detected at about 90° of the incident light are called right-angle light scatter or side scatter. The characteristics of light scatter signals are affected by the size of a cell, the contents of a cell, and the surface properties of a cell.

Preferably, two angles of light scatter signals are used for differentiation of nucleated red blood cells from other cell types. More preferably, one of the light scatter is a low angle light scatter signal which is less than 10°. The preferred range of low angle light scatter signals is from about 0° to about 4°. The second light scatter angle is a low, a medium or a right-angle light scatter signal.

In one example, an experimental flow cytometric instrument was equipped with a multiple angle light scatter detector. The detector detects light scatter signals from a cell passing through a focused flow cell at several ranges of angles, i.e., from about 1° to about 3° (LS1), from about 4° to about 6° (LS2), from about 24° to about 35° (LS3) and higher angles. The instrument was also equipped with a DC impedance detector which can be used together with the light scatter detector to measure light scatter and impedance signals of a cell passing through the flow cell. However, the DC impedance detector can also be turned off when only light scatter measurement is required. An isotonic blood diluent was used as the sheath reagent and a lysing reagent shown in Example 6 was used to lyse the red blood cells.

Figure 4:
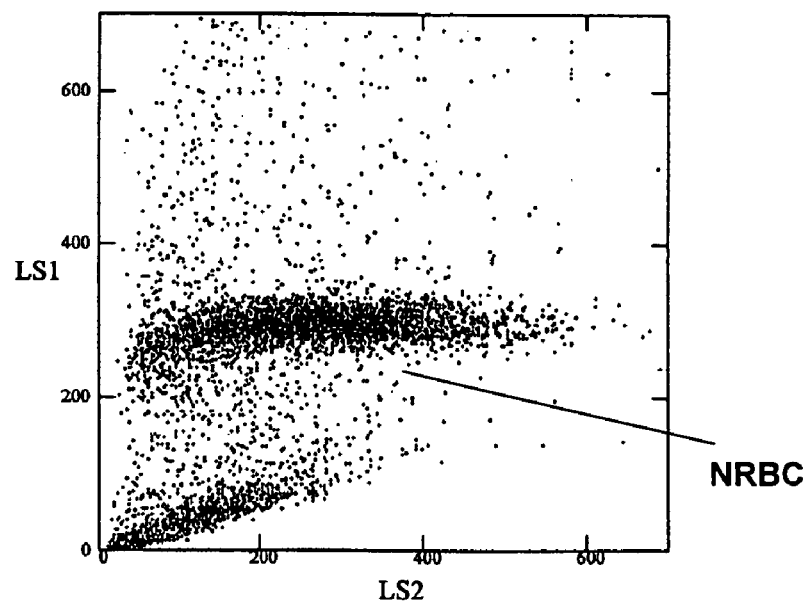
FIG. 4 shows a LS1 vs. LS2 scattergram of a clinical whole blood sample obtained by light scatter measurements.

Example 6 illustrates an example using a reference control composition for measurement of nucleated red blood cells using light scatter measurements. FIG. 4 shows a LS1 vs. LS2 scattergram of a clinical whole blood sample which contained about 100 NRBC per 100 WBC. As shown, the nucleated red blood cells appeared as a distinct cluster, which was separated from the debris (the cluster shown at the bottom of the scattergram), and from white blood cells (above, but out of the range of this scattergram).

Figure 5:
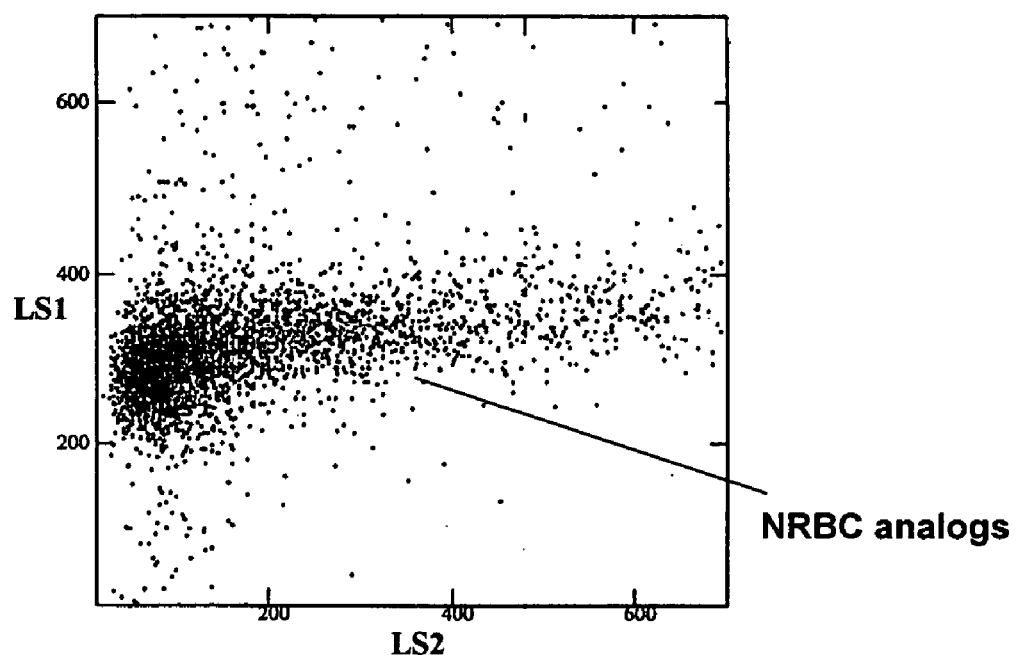
FIG. 5 shows a LS1 vs. LS2 scattergram of a reference control made by mixing the stabilized alligator red blood cells of Example 1 with a fresh human whole blood.
Figure 6:
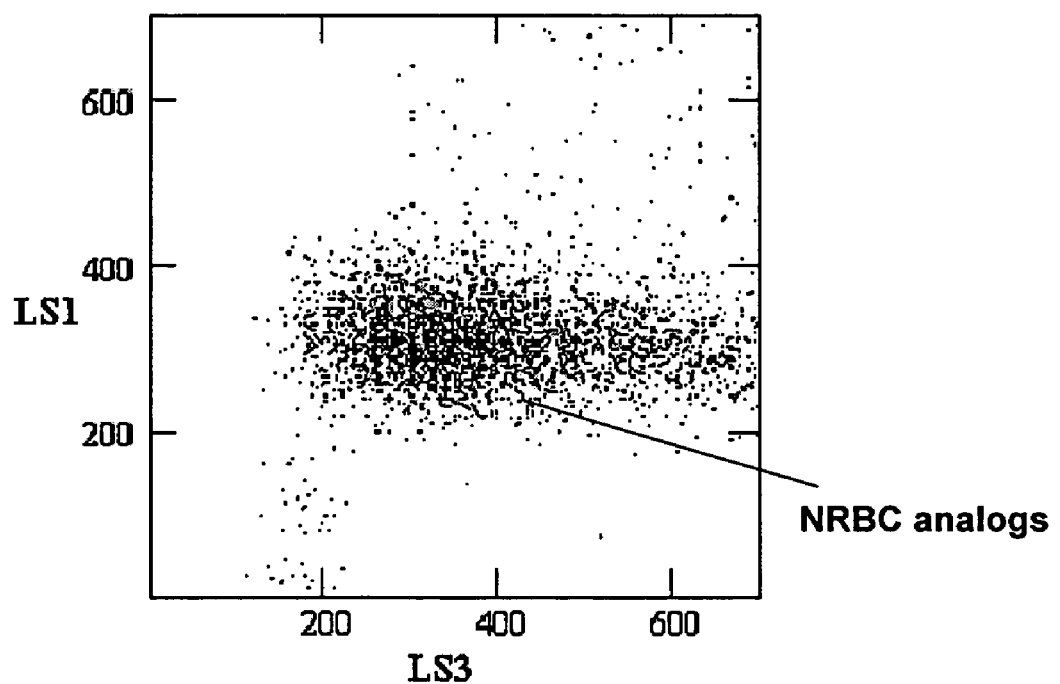
FIG. 6 shows a LS1 vs. LS3 scattergram of a reference control shown in FIG. 5.

FIG. 5 shows a LS1 vs. LS2 scattergram of a reference control composition prepared by mixing a predetermined amount of the stabilized alligator red blood cells of Example 1 with a fresh human whole blood. As shown, the NRBC analogs formed a distinct cluster in the same region of human nucleated red blood cells. Furthermore, FIG. 6 shows a LS1 vs. LS3 scattergram of the same reference control composition.

Figure 7:
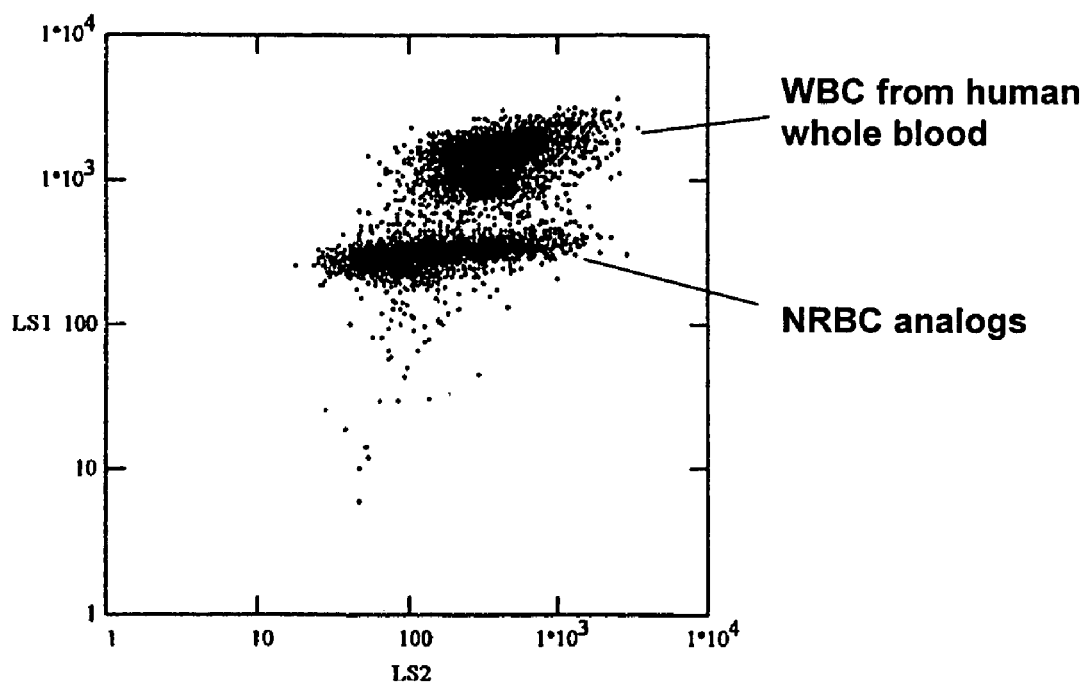
FIG. 7 shows another LS1 vs. LS2 scattergram of the reference control shown in FIG. 5 in log scale with a larger dynamic range.

FIG. 7 shows another LS1 vs. LS2 scattergram in log scale with much larger dynamic range than that shown in FIGS. 4 and 5. As shown, the NRBC analogs were clearly separated from the white blood cells of the human whole blood. Therefore, the reference control composition containing the stabilized alligator red blood cells can be used as the reference control for the differentiation of nucleated red blood cells from other cell types by using low angle light scatter measurements, or by using a combination of low angle and medium angle light scatter measurements.

In a further embodiment, the present invention provides a method of using the reference control composition containing a nucleated red blood cell component for the measurement of nucleated red blood cell using DC impedance and light scatter measurements. The measurement method and instrumentation used for the measurement were also described in U.S. Pat. Nos. 5,874,310 and 5,917,584, which are herein incorporated by reference in their entirety.

Figure 8:
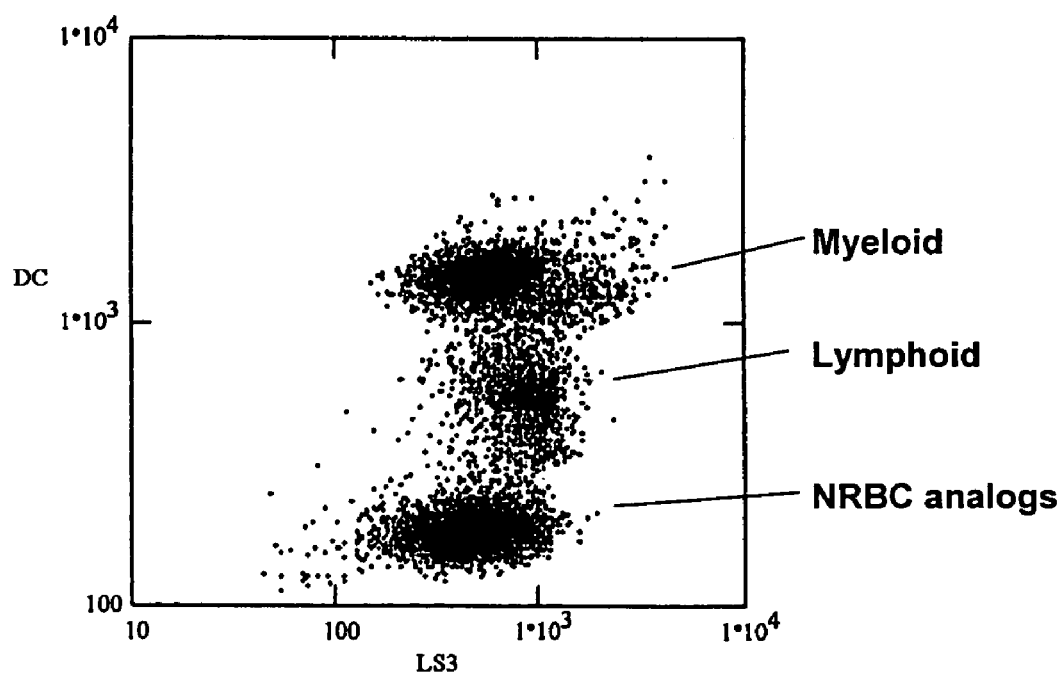
FIG. 8 shows a DC vs. LS3 scattergram of the same reference control shown in FIG. 5.

Example 6 described above further illustrates using a reference control composition for measurement of nucleated red blood cells using DC impedance and light scatter measurements. FIG. 8 shows a DC vs. LS3 scattergram obtained from the same reference control composition shown in FIG. 5. As shown, using the measurements of DC impedance and a medium angle light scatter signal (from about 24° to about 35°), in addition to the differentiation of nucleated red blood cells, the white blood cells were further differentiated into two subpopulations, i.e., myeloid and lymphoid populations.

Therefore, the reference control composition made by mixing the stabilized alligator red blood cells with a fresh human whole blood can be used as the reference control for multiple parameter analyses of a blood sample. With other suitable measurement methods, this reference control composition can be used for differentiation of NRBC from other cell types as well as differentiation of white blood cells into three or five subpopulations.

In yet a further embodiment, the measurement can further include axial light loss measurement. Axial light loss (ALL, also known as forward extinction) is generally the decrease in light energy due to a particle or a cell passing in front of a laser beam and being detected by a photodiode. The light loss is generally due to absorption and scattering, and is defined as the decrease in light energy reaching a detector in the path of the light beam due to the passage of a particle or a cell through that light beam (generally ALL is detected at an angle of from about 0° to about 1°). Different from light scatter signals measured at 0° from the incident light, which is the increase of light due to scattering, the axial light loss is the decrease of light at 0° from the incident light. The optical sensor can be the same for these two measurements, however, the electrical circuitries are different between the two different measurements. In a preferred embodiment, ALL signal is collected in a circular area less than about 0.5° from the incident light axis. ALL is influenced strongly by the particle size. The axial light loss measurement can be used in conjunction with impedance or light scatter measurement.

In another embodiment, the present invention provides a method of using the reference control composition containing a nucleated red blood cell component for the measurement of nucleated red blood cell using a combination of DC impedance and a VCS measurement method. The measurement method and instrumentation used for the measurement are described in U.S. Pat. No. 6,472,215, which is herein incorporated by reference in its entirety. The term of VCS measurement refers a multiple parameter measurement of DC impedance, radio frequency and medium angle light scatter signals, as described in U.S. Pat. No. 5,125,737, which is herein incorporated by reference in its entirety.

Example 7 illustrates an example using a reference control composition for measurement of nucleated red blood cells using a combination of DC impedance and a VCS measurement method. The flow cytometric instrument was a Coulter LH750 hematology analyzer (Beckman Coulter, Inc.), equipped with a non-focused flow aperture and a DC impedance detector for measuring white blood cell count, white blood cell subpopulation and nucleated red blood cells; and a focused flow cell with a VCS detection system for differential analysis of white blood cells and nucleated red blood cells. A blood sample or a reference control was aspirated by the hematology analyzer, and a first aliquot of the sample was lysed and stabilized by the reagents described in Example 7, and delivered to a focused flow cell for differential analysis of white blood cells into five subpopulations. A second aliquot sample was lysed and measured, as it passed through the non-focused flow apertures by the DC impedance detector. The signals acquired from the first aliquot and the second aliquot samples were first analyzed separately and then combined to provide the numbers of nucleated red blood cells.

The reference control composition of Example 3 was analyzed on the LH750 hematology analyzer. The reported numbers of nucleated red blood cells were consistent with the theoretical value of the reference control composition.

The following examples are illustrative of the invention and are in no way to be interpreted as limiting the scope of the invention, as defined in the claims.

EXAMPLE 1

Nucleated Red Blood Cell Component Made of Alligator Red Blood Cells

The following is a specific example of preferred reagents and recommended specific procedural steps for treating alligator red blood cells to obtain a nucleated red blood cell component or NRBC analog.

| Phosphate Buffered Saline Solution (PBS) Liter Formulation | |
|---|---|
| 1. Sodium phosphate monobasic: | 0.2 g |
| 2. Sodium phosphate dibasic 7H$_2$O: | 2.0 g |
| 3. Sodium azide: | 0.1 g |
| 4. Sodium chloride: | 9.4 g |
| 5. Qs to 1 liter with distilled water: | pH approximately 7.4; osmolality 315 to 345 mOsm/kg. |

| A First Stabilizing Suspension Medium Approximate Amounts Liter Formulation | |
|---|---|
| 1. Distilled water | 500 ml |
| 2. Propyl paraben | 0.3 to 1.0 gm |
| 3. Methyl paraben | 0.5 to 1.0 gm |
| 4. Procaine hydrochloride | 0.1 to 0.5 gm |
| 5. Deoxycholic acid | 0.1 to 0.9 gm |
| 6. Lactose | 10.0 to 50.0 gm |
| 7. Actidione | 0.1 to 0.6 gm |
| 8. Trisodium citrate dehydrate | 3.0 to 8.0 gm |
| 9. Citric acid monohydrate | 0.3 to 0.9 gm |
| 10. Sodium dihydrogen phosphate monohydrate | 0.8 to 2.5 mg |
| 11. Phenergan hydrochloride | 0.1 to 1.0 gm |
| 12. Colistimethate, sodium | 0.2 to 0.9 gm |
| 13. Penicillin G., sodium | $0.5 \times 10^6$ to $3 \times 10^6$ units |
| 14. Kanamycin sulfate | 0.2 to 0.8 gm |
| 15. Neomycin sulfate | 0.2 to 1.0 gm |
| 16. 5'-AMP | 0.4 to 1.0 gm |
| 17. Adenine | 0.2 to 0.8 gm |
| 18. Inosine | 0.4 to 1.0 gm |
| 19. Dihydrostreptomycin sulfate | 0.2 to 1.0 gm |
| 20. Tetracycline hydrochloride | 0.2 to 1.0 gm |
| 21. 30% Bovine albumin | 100 to 350 ml |
| 22. q.s. to 1 liter with distilled water | |

| A Second Stabilizing Suspension Medium Approximate Amounts Liter Formulation | | |
|---|---|---|
| Component | Range (grams/liter) | Preferred Range (grams/liter) |
| Xanthine compound | 1–10 | 2–7 |
| Adenosine monophosphate | 0.1–1.0 | 0.2–0.8 |
| Inosine | 0.1–1.0 | 0.2–0.8 |
| pH adjusting agents sufficient to obtain | pH 5.8–6.8 | pH 6.0–6.5 |
| Osmolality adjusters sufficient to obtain | 200–400 mOsm | 250–350 |
| Preservative | effective amount | 2.0–6.0 |
| Water | fill to 1 liter | |

Procedure:

1. Select alligator red blood cells having a mean cell volume range of about 380 to 460 fl. Centrifuge the alligator whole blood and remove the top layer (including white blood cells, platelets and plasma).

2. Wash the packed alligator red blood cells with the phosphate buffered saline solution (PBS), usually three times.

3. Resuspend the washed alligator red blood cells in one of the above-described stabilizing suspension media. The stabilized alligator red blood cells can be stored at about 4° C. for a time period in excess of 45 days.

EXAMPLE 2

Reference Control Composition Containing a Nucleated Red Blood Cell Component, a White Blood Cell Component, and Red Blood Cell and Platelet Components Procedure:

1. Provide a predetermined volume of the first suspension medium described in Example 1.

2. Add a predetermined amount of stabilized human red blood cells in the medium. The stabilized human red blood cells were processed following the procedure described in U.S. Pat. Nos. 4,299,726 and 4,358,394.

3. Add a predetermined amount of platelet analogs in the suspension medium containing the stabilized human red blood cells. The platelet analogs were made of fixed goat red blood cells following the procedure described in U.S. Pat. Nos. 4,264,470, 4,389,490 and 4,405,719.

4. Add a predetermined amount of fixed goose red blood cells as the white blood cell component into the suspension medium containing the stabilized human red blood cells and platelet analogs.

5. Add a predetermined amount of stabilized alligator red blood cells of Example 1 into the suspension medium containing the stabilized human red blood cells, platelet analogs and white blood cell component.

6. Mixing the reference control composition formed in step 5. The cell concentrations of the red blood cell, white blood cell and platelet components were prepared to simulate the corresponding cell concentrations of a human whole blood sample. The cell concentration of the nucleated red blood cell component was prepared to simulate a clinical sample containing certain level of nucleated red blood cells, preferably in a range of 1 to 50 NRBCs per 100 WBC. The reference control composition can be stored at about 4° C. for a time period in excess of 45 days.

EXAMPLE 3

Hematology Reference Control Composition Containing a Nucleated Red Blood Cell Component, and Multiple White Blood Cell Subcomponents The procedure for making this reference control composition was essentially the same as the procedure described above in Example 2, except that in step 4 predetermined amounts of multiple white blood cell subcomponents were added into the suspension medium containing the stabilized human red blood cells and platelet analogs. The reference control composition can be stored at about 4° C. for a time period in excess of 45 days.

The multiple white blood cell subcomponents were prepared following the procedures described in U.S. Pat. Nos. 4,704,364, 5,320,964 and 5,512,485. Using the multiple white blood cell analogs prepared following the procedures described in U.S. Pat. No. 4,704,364, the reference control composition can be used for nucleated red blood cell measurement and differentiation of white blood cells into three subpopulations. Using the multiple white blood cell analogs prepared following the procedures described in U.S. Pat. Nos. 5,320,964 and 5,512,485, the reference control composition can be used for nucleated red blood cell measurement and differentiation of white blood cells into five subpopulations.

EXAMPLE 4

Linearity Control Containing a Nucleated Red Blood Cell Component

The procedure of Example 2 was used to prepare the linearity control. In step 5, aliquot a constant predetermined volume of the suspension containing stabilized human red blood cells, platelet analogs and white blood cell component into a series of containers, then add a series of predetermined amounts of stabilized alligator red blood cells prepared in Example 1 into these containers. The concentration of the white blood cell component was kept constant at about $10 \times 10^3/\mu L$ and the NRBC analog concentration varied in a range to produce a ratio of the NRBC analog to the WBC analogs between 0 to about 45 NRBCs per 100 WBC. The reference control compositions contained about $4.7 \times 10^6/\mu L$ of stabilized human red blood cells and about $2.2 \times 10^5/\mu L$ of platelet analog.

EXAMPLE 5

Use of the Reference Control Composition on a Flow Cytometric Instrument for Measurement of Nucleated Red Blood Cells Using a DC Impedance Measurement An experimental lysing reagent was prepared, which was an aqueous solution containing active components for lysing red blood cells and analysis of nucleated red blood cells: 25.0 g/L of tetradecyltrimethylammonium bromide, 15.0 g/L of Igepal SS-837 (ethoxylated phenol, from Rhone-Poulenc, Cranbury, N.J.), and 4.0 g/L Plurofac A38 prill surfactant (ethoxylated alcohol, from BASF Corp., Mount Olive, N.J.).

An aliquot of a whole blood sample or a reference control composition was aspirated by a modified Coulter LH750 hematology analyzer (Beckman Coulter, Inc. Miami, Fla.), equipped with non-focused flow apertures and a DC-impedance detector for measuring white blood cell count, white blood cell subpopulations and nucleated red blood cells. The aspirated sample was diluted with an isotonic blood diluent, LH700 Series Diluent (product of Beckman Coulter, Inc.), then mixed with a volume of the above described lytic reagent composition. The sample mixture was drawn through a set of three apertures by a vacuum source. Each blood cell was measured, as it passed through the apertures, by the DC impedance detector. The measurement was performed at a temperature in the range of about 18° to about 28° C.

FIG. 1 is an obtained histogram of a clinical whole blood sample which contained about 22 NRBCs per 100 WBC. As shown, the nucleated red blood cells appeared as a distinct peak on the left of the histogram and white blood cells appeared on the right side of the nucleated red blood cells.

FIG. 2 is the obtained histogram of the reference control composition of Example 2. As shown, the stabilized alligator red blood cells closely resembled human nucleated red blood cells and they were clearly separated from the WBC analog. The obtained histogram was post analyzed, and the ratio between the NRBC analog and the WBC analog was reported as numbers of NRBC per 100 WBC.

The linearity control of Example 4 was measured on the modified LH750 hematology analyzer following the process described above. Each of six control compositions containing 0 to 45 NRBC per 100 WBC was aspirated and analyzed by the analyzer. The numbers of NRBC per 100 WBC obtained from the histograms were plotted against the theoretical values obtained from the NRBC analog and WBC analog concentrations. FIG. 3 is the obtained correlation curve. As shown, the measured NRBC concentrations of the reference control compositions had an excellent linear correlation with the theoretical values within the concentration range measured.

EXAMPLE 6

Use of the Reference Control Composition on a Flow Cytometric Instrument for Measurement of Nucleated Red Blood Cells Using Light Scatter Measurement, and Light Scatter and DC Impedance Measurements An experimental lysing reagent was prepared, which was an isotonic aqueous solution containing: 14 g/L of $Na_2SO_4$, 2 g/L of NaCl, 2 g/L of triazole, 9 g/L of dodecyltrimethylammonium chloride (from AKZO, Chicago, Ill.), 0.5 g/L of tetradecyltrimethylammonium bromide, and having a pH of 7.

An aliquot of a whole blood sample or a reference control composition was mixed with an amount of the above described lytic reagent composition with a dilution ratio of 30:1. 20 seconds after the addition of the lytic reagent, the sample mixture was delivered to a flow cell with a sheath fluid, ISOTON® III diluent (product of Beckman Coulter, Inc.) on an experimental hematology instrument. The experimental hematology instrument was equipped with an optical detector enabling detection of light scatter signals at various angles from about 1° to about 3° (LS1), from about 4° to about 6° (LS2), from about 24° about 35° (LS3) and higher angles, as well as a DC impedance detector. Each blood cell was measured, as it passed through a focused flow cell, by the detectors. The DC impedance detector can be used together with the light scatter detector, and it can also be turned off when only light scatter measurement is required. The measurement was performed at a temperature in the range of about 18° to about 28° C.

FIG. 4 is an obtained LS1 vs. LS2 scattergram of a clinical whole blood sample which contained about 100 NRBCs per 100 WBC. As shown, the nucleated red blood cells appeared as a distinct cluster, which was separated from the debris (the cluster shown at the bottom of the scattergram), and from white blood cells (above, but out of the range of this scattergram).

FIG. 5 is an obtained LS1 vs. LS2 scattergram of a reference control composition prepared by adding and mixing an amount of the stabilized alligator red blood cells of Example 1 with a fresh human whole blood. As shown, the NRBC analogs formed a distinct cluster in the same region of human nucleated red blood cells. FIG. 6 is an obtained LS1 vs. LS3 scattergram of the reference control composition.

FIG. 7 is another LS1 vs. LS2 in log scale with much larger dynamic range than that shown in FIG. 4 and FIG. 5. As shown, the NRBC analogs were clearly separated from the white blood cells of the human whole blood.

FIG. 8 is an obtained DC vs. LS3 scattergram of the same reference control composition shown in FIG. 5. As shown, using the measurements of DC and LS3, in addition to the differentiation of nucleated red blood cells, the white blood cells were further differentiated into two subpopulations, i.e., myeloid and lymphoid populations.

EXAMPLE 7

Use of the Reference Control Composition on a Flow Cytometric Instrument for Measurement of Nucleated Red Blood Cells Using DC Impedance and VCS Measurements The flow cytometric instrument was a Coulter LH750 hematology analyzer (Beckman Coulter, Inc.), equipped with non-focused flow apertures and a DC-impedance detector for measuring white blood cell count, white blood cell subpopulations and nucleated red blood cells, and a focused flow cell with a VCS detection system. The VCS detection system measures the DC impedance, radio frequency and medium angle light scatter signals of a cell passing through the flow cell.

A blood sample or a reference control composition was aspirated by the hematology analyzer, and a first aliquot of the sample was mixed with an amount of a first lytic reagent, Erythrolyse® II, to lyse red blood cells and subsequently mixed with an amount of a stabilizing reagent, Stabilyse, (both are products of Beckman Coulter, Inc.). The first sample mixture was delivered to the focused flow cell for differential analysis of white blood cells into five subpopulations, and nucleated red blood cell analysis. The second aliquot of the sample was diluted with an isotonic blood diluent, LH700 Series Diluent, then mixed with an amount of a second lytic reagent, Lyse S® III (both are products of Beckman Coulter, Inc.). The sample mixture was drawn through a set of three apertures by a vacuum source. Each blood cell was measured, as it passed through the apertures by the DC impedance detector. The measurement was performed at a temperature in the range of about 18° to about 28° C. The signals acquired from the first aliquot and the second aliquot samples were first analyzed separately, and then combined to provide the numbers of nucleated red blood cells.

The reference control composition of Example 3 was analyzed on the LH750 hematology analyzer. The reported numbers of nucleated red blood cells were consistent with the theoretical values of the reference control composition.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A method of using a reference control composition for measurement of nucleated red blood cells comprising the steps of:
   (a) providing a reference control composition to a flow cytometric instrument, said reference control composition comprising a nucleated red blood cell component made of stabilized animal nucleated red blood cells; wherein said stabilized animal nucleated red blood cells have impedance properties simulating impedance properties of human nucleated red blood cells under a blood lysing condition as measured by an impedance measurement;
   (b) mixing said reference control composition with a lytic reagent to form a control sample mixture; wherein upon exposing to said lytic reagent said stabilized animal nucleated red blood cells are substantially lysed and cellular volume thereof reduce to substantially nuclear volume;
   (c) measuring said control sample mixture by said impedance measurement to measure said substantially lysed animal nucleated red blood cells from step (b);
   (d) performing an analysis of signals obtained from said impedance measurement in step (c) and obtaining numbers of simulated human nucleated red blood cells from said analysis; and
   (e) reporting said numbers of simulated human nucleated red blood cells in said reference control composition.

2. The method of claim 1, wherein said impedance measurement is a direct current (DC) impedance measurement.

3. The method of claim 1, wherein said impedance measurement is a radio frequency (RF) impedance measurement.

4. The method of claim 1, wherein said stabilized animal nucleated red blood cells have a mean cell volume from about 380 fl to about 460 fl.

5. The method of claim 4, wherein said stabilized animal nucleated red blood cells are one selected from the group consisting of reptile red blood cells and fish red blood cells.

6. The method of claim 4, wherein said stabilized animal nucleated red blood cells are alligator red blood cells.

7. The method of claim 1, where said reference control composition further comprises a white blood cell component in a suspension medium, and said method further comprises measuring and reporting white blood cells.

8. The method of claim 7, where said reference control composition further comprises a red blood cell component and a platelet component dispersed in said suspension medium, and said method further comprises measuring and reporting red blood cells and platelets.

9. A method of using a reference control composition for measurement of nucleated red blood cells comprising the steps of:
   (a) providing a reference control composition to a flow cytometric instrument, said reference control composition comprising a nucleated red blood cell component made of stabilized animal nucleated red blood cells; wherein said stabilized animal nucleated red blood cells have impedance and optical properties simulating impedance and optical properties of human nucleated red blood cells under a blood lysing condition as measured by direct current (DC) impedance and axial light loss measurements;
   (b) mixing said reference control composition with a lytic reagent to form a control sample mixture; wherein upon exposing to said lytic reagent said stabilized animal nucleated red blood cells are substantially lysed and cellular volume thereof reduce to substantially nuclear volume;
   (c) measuring said control sample mixture by said DC impedance and axial light loss measurements to measure said substantially lysed animal nucleated red blood cells from step (b);
   (d) performing an analysis of signals obtained from said DC impedance and axial light loss measurements in step (c) and obtaining numbers of simulated human nucleated red blood cells from said analysis; and (e) reporting said numbers of simulated human nucleated red blood cells in said reference control composition.

10. The method of claim 9, wherein said stabilized animal nucleated red blood cells have a mean cell volume from about 380 fl to about 460 fl.

11. The method of claim 10, wherein said stabilized animal nucleated red blood cells are one selected from the group consisting of reptile red blood cells and fish red blood cells.

12. The method of claim 10, wherein said stabilized animal nucleated red blood cells are alligator red blood cells.

13. The method of claim 9, where said reference control composition further comprises a white blood cell component in a suspension medium, and said method further comprises measuring and reporting white blood cells.

14. The method of claim 9, where said reference control composition further comprises a red blood cell component and a platelet component, and said method further comprises measuring and reporting red blood cells and platelets.

15. A method of using a reference control composition for quantitative measurement of nucleated red blood cells comprising the steps of:

(a) providing a reference control composition comprising a nucleated red blood cell component made of stabilized animal nucleated red blood cells; wherein said stabilized animal nucleated red blood cells have DC impedance, radio frequency, and light scatter properties simulating DC impedance, radio frequency, and light scatter properties of human nucleated red blood cells under a blood lysing condition as measured by DC impedance, radio frequency, and light scatter measurements;

(b) exposing a first aliquot of said reference control composition to a first lysing reagent system to lyse red blood cells and to form a first control sample mixture;

(c) exposing a second aliquot of said reference control composition to a second lysing reagent system to lyse red blood cells and to form a second control sample mixture; wherein upon exposing to said first and second lytic reagent systems said stabilized animal nucleated red blood cells are substantially lysed and cellular volume thereof reduce to substantially nuclear volume;

(d) measuring said first control sample mixture in a flow cell by a detection comprising a first direct current impedance measurement (DC1), radio frequency impedance measurement (RF), and a median angle light scatter measurement (LS);

(e) measuring blood cell distributions of said second control samp by a second direct current impedance measurement (DC2);

(f) performing an analysis of signals obtained from said measurements of steps (d) and (e), and obtaining numbers of simulated human nucleated red blood cells from said analysis; and (g) reporting numbers of said simulated nucleated red blood cells in said reference control composition.

16. The method of claim 15, wherein said stabilized animal nucleated red blood cells have a mean cell volume from about 380 fl to about 460 fl.

17. The method of claim 16, wherein said stabilized animal nucleated red blood cells are one selected from the group consisting of reptile red blood cells and fish red blood cells.

18. The method of claim 16, wherein said stabilized animal nucleated red blood cells are alligator red blood cells.

19. The method of claim 15, where said reference control composition further comprises a white blood cell component in a suspension medium, and said method further comprises measuring and reporting white blood cells.

20. The method of claim 15, where said reference control composition further comprises a red blood cell component and a platelet component, and said method further comprises measuring and reporting red blood cells and platelets.

21. A reference control composition comprising a predetermined volume of an analog suspension comprising stabilized unfixed animal nucleated red blood cells suspended in a suspension medium, and a predetermined volume of an unfixed human whole blood, wherein said suspension medium is compatible with said human whole blood such that blood cells of said human whole blood in said composition behave substantially the same to blood cells of said human whole blood prior to mixing with said analog suspension in an analysis on a flow cytometric instrument.

22. The reference control composition of claim 21, wherein said animal nucleated red blood cells are one selected from the group consisting of reptile and fish red blood cells.

* * * * *